United States Patent
Sun

(10) Patent No.: US 6,712,840 B2
(45) Date of Patent: Mar. 30, 2004

(54) TUMOR ELECTROCHEMICAL-THERAPEUTIC DEVICE USING ELECTROTHERMAL NEEDLES

(76) Inventor: Caijin Sun, Si Jing Li 4-2-402 Feng Qi Road, Hang Zhou City, Zhejiang Province (CN), 310006

( * ) Notice: Subject to any disclaimer, the term of this patent is extended or adjusted under 35 U.S.C. 154(b) by 0 days.

(21) Appl. No.: 10/047,634

(22) Filed: Oct. 23, 2001

(65) Prior Publication Data

US 2003/0125784 A1 Jul. 3, 2003

(30) Foreign Application Priority Data

Apr. 23, 1999 (CN) .......................... 99104583 A

(51) Int. Cl.[7] .............. A61F 7/00; A61B 18/04
(52) U.S. Cl. .......... 607/96; 607/99; 607/113; 606/34
(58) Field of Search ............ 606/34, 36, 41, 606/42, 43, 44, 46, 48; 607/96, 98, 99, 113

(56) References Cited

U.S. PATENT DOCUMENTS 5,674,267 A * 10/1997 Mir et al. .............. 607/72
6,009,347 A * 12/1999 Hofmann .............. 604/21
6,190,383 B1 * 2/2001 Schmaltz et al. ........ 606/41
6,451,002 B1 * 9/2002 Dev et al. .............. 604/500

FOREIGN PATENT DOCUMENTS

| CN | 2057590 | 5/1990 |
| CN | 1163150 | 10/1997 |
| WO | 9739793 | 10/1997 |

* cited by examiner

*Primary Examiner*—Roy D. Gibson
(74) *Attorney, Agent, or Firm*—Baker Botts L.L.P.

(57) ABSTRACT

A cancer electrochemical-therapeutic device using electrothermal needles, comprising two groups of electrothermal needles and three D.C. power supplies, each group having at least one electrothermal needle, two of the three D.C. power supplies—serving as heating power supply—being connected to the groups of electrothermal needles to heating them to realize electrothermal therapy, and the other D.C. power supply—serving as electrochemical power supply—being connected to the corresponding electrodes of the D.C. power supplies to realize electrochemical therapy between two electrothermal needles. The device is simple, easy to use and reliable, its cost is low and its therapy effect is good.

7 Claims, 1 Drawing Sheet

TUMOR ELECTROCHEMICAL-THERAPEUTIC DEVICE USING ELECTROTHERMAL NEEDLES

FIELD OF THE INVENTION

This application is a continuation and claims the benefit of International Patent Application No. PCT/CN00/00073 filed Apr. 3, 2000, published in Chinese as WO 00/64532, which claims priority to Chinese Patent Application No. 99104583.1 of Caijun Sun entitled "CANCER ELECTROCHEMICAL-THERAPEUTIC DEVISE USING ELECTROTHERMAL NEEDLES" filed on Apr. 23, 1999. The present invention relates to a device which is a kind of therapy instrument, in which electrothermal needles are used as electrodes for tumor electrochemical therapy, whereby electrothermal therapy can be effected in addition.

BACKGROUND OF THE INVENTION

Electrothermal needles and electrochemistry techniques have been used separately for tumor therapy for more than ten years. The current that is produced after switching on the power supply is used by both techniques, on the one hand, for activating the heating body within the hollow body of the electrothermal needle to produce heat and effecting the heat on the tumor focus tissue where the electrothermal needles are inserted, and on the other hand, for activating both the positive and negative electrodes which are inserted into the tumor focus so that the electrode reaction and the electrode sub-reaction occur between both the positive and negative electrodes, and concentrated acid and alkali killing regions are produced respectively between both electrodes to achieve the result of the electrochemistry therapy. Because these two techniques for tumor therapy are used separately in clinic, the temperature of the therapy in which only the electrothermal needles for treating the tumor focus are used is difficult to control. In particular, the temperature can not be increased evenly when the diameter of the tumor tissue is large. Although tumor cells can be killed by using electrochemistry therapy only, problems, such as uneven heating, as well as being unable to synchronize, etc., still exist.

SUMMARY OF THE INVENTION

The object of the invention is to overcome the above disadvantages by being aimed at utilizing the features of the coordination, supplement, and effectiveness of electrothermal needles and electrochemical-therapy techniques at the effective mechanism of physics, chemistry, and biology to integrate effectively the electrothermal needles and the electrochemical-therapeutic techniques as a whole to provide a tumor electrochemical-therapeutic device using electrothermal needles.

The object of the invention is realized by using the following technical scheme. It is constructed by at least two groups of electrothermal needles and three D.C. power supplies, wherein, at least one electrothermal needle within which a heating body is placed is involved in each group; wherein two of the three D.C. power supplies connected respectively to the heating bodies within the two groups of electrothermal needles are used as the heating power supplies, and the other power supply is used as the electrochemical power supply with its two electrodes connected respectively to the corresponding electrodes of two heating power supplies.

The electrothermal needle of the invention includes a group of center electrothermal needles comprising at least one electrothermal needle, and a group of surrounding electrothermal needles comprising at least two electrothermal needles. The center electrothermal needle has a heating power supply with its one electrode (e.g. positive electrode) connected to the same electrode (e.g. the positive electrode) of the electrochemical power supply, and the another corresponding electrode (e.g. the negative electrode) of the heating power supply for the surrounding electrothermal needle is connected to another same electrode (e.g. the negative electrode) of the electrochemical power supply.

Both the heating power supply and the electrochemical power supply are floating D.C. constant current adjustable power supplies, wherein the magnitude of electrochemical current can be adjusted by the electrochemical power supply and the heating temperature of electrothermal needle can be adjusted by the heating power supply.

The electrothermal needle of the invention is a hollow needle body made of stainless steel, with a heating body made of nichrome filament placed inside, and the center electrothermal needle is coated with platinum.

A temperature detection needle is also provided in the invention, it is constructed by inserting and isolating a thermal sensor for detecting the temperature into and from the hollow needle body made of stainless steel, and a temperature indicator is connected to the thermal sensor for detecting the temperature.

DESCRIPTION OF THE PREFERRED EMBODIMENTS

Figure 1:
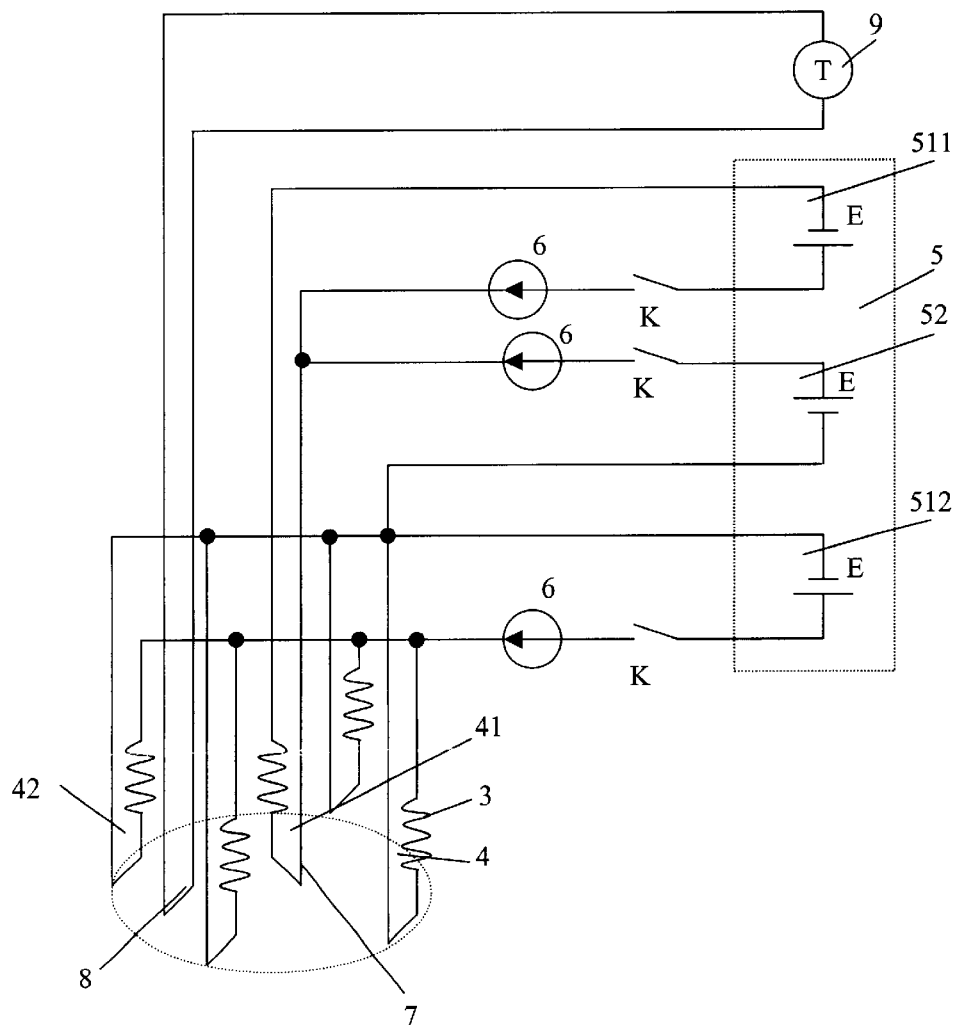
FIG. 1 is a schematic view of the structure of the invention.
Figure 2:
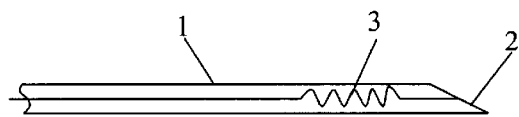
FIG. 2 is a schematic view of the structure of the electrothermal needle of the invention.

The invention will be explained from the detailed description set forth below when taken in conjunction with the drawings. As shown in FIG. 2, the electrothermal needle structure of the invention includes a stainless steel hollow needle body 1; a sharp needle head part 2 at the front end of the needle body 1; and a heating body 3 made of the nichrome filament, one end of which is connected to the sharp needle head part 2, and the other end is connected to an electrode of the power supply. Another electrode of the power supply is connected to the needle body 1 to form a current loop. After the current flowing through the heating body 3, the heat will be produced. Since the above structure of the electrothermal needle has been published on the Chinese Patent Document as a known technology, it will not be explained in detail herein. As shown in FIG. 1, the present embodiment comprises mainly five electrothermal needles 4 with the heating body 3 placed inside, and three floating D.C. constant current adjustable power supplies 5 which are separated from each other. The electrothermal needles 4 are divided into two groups, a center electrothermal needle 41 is constructed by one electrothermal needle in one group, and the surrounding electrothermal needles 42 is constructed by four electrothermal needles in another group; two power supplies in the power supply 5 are the heating power supplies 511, wherein two electrodes of the heating power supply 511 are connected to the center electrothermal needle, and two electrodes of the other heating power supply 512 are connected in parallel to four surrounding electrothermal needles; another power supply the power supply 5 is the electrochemical power supply 52, the positive electrode of which is connected to the positive electrode of the heating power supply 511, and the negative electrode of which is connected to the negative electrode of the heating power supply 512. In another embodiment of the invention, the positive and negative electrodes of the electrochemical power supply can be connected in a reverse fashion. That is, the positive electrode of which can be connected to the positive electrode of the heating power supply 512, and the negative electrode of which can be connected to the negative electrode of the heating power supply 511. In the loop of the above power supply 5, switches K and current adjusters 6 are also deposed, so that the temperature of the electrothermal needles can be controlled by adjusting the heating current; as well as the magnitude of the electrochemical current I can be achieved by adjusting the current adjuster 6. When operating, the heating power supply is switched on, so that the heat will be produced by the center electrothermal needle 41 and the surrounding electrothermal needle 42, and the heat effect to the tumor will be occurred. When only the electrochemical power supply 52 is switched on, the current will be produced between the center electrothermal needle 41 and the surrounding electrothermal needle 42, that is, the electrochemical-therapeutic effect will be produced between the electrothermal needles 4, and the chemical reaction will occur in the tumor tissue, that is, the concentrated acid and alkali regions are produced at one end and the other end of the electrothermal needles. When the heating power supply 511 and the electrochemical power supply 52 are switched on at the same time, the tumor tissue is effected by the electrothermal therapy effect and the electrochemical therapy effect produced by both of them simultaneously, so that the killing effect to the tumor tissue can be increased.

The structure of the center electrothermal needle 41 described in the invention is similar as that of the surrounding electrothermal needle 42, but it is coated with platinum 7 for avoiding the corrupting effect of the chemical procedure.

A temperature detection needle 8 is also provided in the invention. It is constructed by inserting and isolating a thermal sensor for detecting the temperature into and from the hollow needle body made of stainless steel, and a temperature indicator is connected to the thermal sensor for detecting the temperature.

The center electrothermal needle 41 may be substituded by an electrode needle made of a platinum filament.

Another embodiment of the invention includes the center electrothermal needle 41 which is comprised of two or more electrothermal needles 4 and the surrounding electrothermal needle 42 which is comprised of three or more electrothermal needles. The power supply 5 may be comprised of several heating power supplies 511 to form heating power supply group, or may be comprised of several electrochemical power supplies 52 to form electrochemical power supply group. Switching on the heating body 3 within the electrothermal needle 4 and producing heat thereof is mainly used by the invention to produce the electrothermal therapy effect; two electrothermal needles are used as both the positive and the negative electrodes of the power supply, then the current will be produced so that electrochemical therapy effect will be occurred in the tumor tissue.

Because in the invention, a group of the electrothermal needles heating internally is used as one electrode which is inserted into the tumor tissue from the periphery of the tumor focus; and an electrothermal needle which is coated with the platinum is used as another electrode to insert into the center of the tumor focus. When the constant current is applied to each needle, the electrode reaction and the electrode sub reaction occur between the cathode and the anode where the electrode is their shaft, and concentrated acid and alkali killing regions are produced, respectively. The killing effect of these killing substances can be increased under the heat effect. According to the law of the chemical dynamics, as the temperature of the chemical reaction system increases per 10° C., the reaction speed will increase 2–3 times, so that the therapy result will be improved significantly. Additionally, the enhanced dissolution effect of the acid (HCl, pH 2–3) formed in the anode region and the alkali (NaOH, pH 12–13) formed in the cathode region will enlarge and increase the space and the canal between the cells, the heat and the killing substances produced at the electrodes of the electrothermal needles can be spread quickly to nearby regions by the above effect, so that the unevenness of the therapy that occurred while utilizing separately the electrothermal therapy and the electrochemical therapy can be improved significantly. Moreover, after cooperating both therapies, the killing effect of the cells, the coagulation effect of the blood, and the systolic effect of the blood vessels will be enhanced by the electrochemical therapy; and the possibility of the tumor cells transferring caused by the expansion of the tissue volume, the looseness of the cell connection, the expansion of the blood vessel, and the increase in the blood flow rate which are caused by the heat effect will also be decreased. Finally, the therapy dosage will be less than that of the two therapies used separately, the therapy period will decrease, and the patient's pain will decrease. Two therapy functions are integrated by the invention. They can be used separately or integrally, as well as one function can be used before or after the other one, and thus the therapy result of the entire instrument increases significantly, but the cost of the entire instrument have not been increased.

I claim:

1. A tumor electrothermal and electrochemical-therapeutic device comprising:
    a first group of one or more electrothermal needles each comprising a heating body;
    a second group of two or more electrothermal needles each comprising a heating body; and
    three direct current power sources each comprising at least one positive terminal and at least one negative terminal,
wherein
    the first direct current power source is a heating power supply, the positive and negative terminals of which are operatively electrically coupled with the electrothermal needles in the first group;
    the second direct current power source is a heating power supply, the positive and negative terminals of which are operatively electrically coupled with the electrothermal needles in the second group; and
    the third direct current power source is an electrochemical power supply, the positive terminal of which is operatively electrically connected to the positive terminal of one of said heating power supplies and the negative terminal of which is operatively electrically connected to the negative terminal of the other heating power supply.

2. The tumor electrothermal and electrochemical-therapeutic device of claim 1, wherein said first group of electrothermal needles is centrally positioned with respect to said second group of electrothermal needles.

3. The tumor electrothermal and electrochemical-therapeutic device of claim 2, wherein the direct current power sources are floating direct current constant current adjustable power supplies wherein the magnitude of electrochemical current can be adjusted by the electrochemical power supply, and the heating temperature of electrothermal needles can be adjusted by the heating power supply.

4. The tumor electrothermal and electrochemical-therapeutic device of claim 1, wherein said electrothermal needles each comprise a hollow stainless steel needle body.

5. The tumor electrothermal and electrochemical-therapeutic device of claim 4, wherein said electrothermal needles each further comprises a nichrome filament heating body in the hollow of said stainless steel needle body.

6. The tumor electrothermal and electrochemical-therapeutic device of claim 2, wherein each electrothermal needle of the first group of electrothermal needles further comprises a platinum coating.

7. The tumor electrothermal and electrochemical-therapeutic device of claim 1 further comprising:

a temperature detection needle comprising a hollow stainless steel needle body and a thermal sensor; and a temperature indicator, wherein the thermal sensor is in the hollow of said stainless steel needle body, electrically insulated from said stainless steel needle body, and operatively connected to the temperature indicator.

* * * * *

UNITED STATES PATENT AND TRADEMARK OFFICE
CERTIFICATE OF CORRECTION

PATENT NO.    : 6,712,840 B2
DATED         : October 5, 2004
INVENTOR(S)   : Sun, Caijun It is certified that error appears in the above-identified patent and that said Letters Patent is hereby corrected as shown below:

Title page,
Item [76], Inventors, "Caijin Sun" should read -- Caijun Sun --

Column 2,
Line 58, "needles is" should read -- needles are --

Column 3,
Line 44, "substituded" should read -- substituted --

Signed and Sealed this

Thirtieth Day of November, 2004

JON W. DUDAS
*Director of the United States Patent and Trademark Office*